(12) United States Patent
Burger

(10) Patent No.: US 7,874,294 B2
(45) Date of Patent: Jan. 25, 2011

(54) DEVICE FOR PREVENTING BRUXISM

(75) Inventor: Michael Albertus Burger, Eindhoven (NL)

(73) Assignee: Bruxtec B.V., Uden (NL)

( * ) Notice: Subject to any disclaimer, the term of this patent is extended or adjusted under 35 U.S.C. 154(b) by 713 days.

(21) Appl. No.: 10/585,826

(22) PCT Filed: Dec. 21, 2004

(86) PCT No.: PCT/NL2004/000895
§ 371 (c)(1),
(2), (4) Date: Oct. 12, 2007

(87) PCT Pub. No.: WO2005/067833
PCT Pub. Date: Jul. 28, 2005

(65) Prior Publication Data
US 2008/0115792 A1 May 22, 2008

(30) Foreign Application Priority Data
Jan. 13, 2004 (NL) .................... 1025223

(51) Int. Cl.
*A61F 5/56* (2006.01)
(52) U.S. Cl. .................... 128/848; 600/587; 600/590
(58) Field of Classification Search .......... 128/848; 600/393, 590, 587, 586; 607/47, 134
See application file for complete search history.

(56) References Cited

U.S. PATENT DOCUMENTS

| 5,078,153 A | | 1/1992 | Burman et al. |
| 5,265,624 A | | 11/1993 | Bowman |
| 5,490,520 A | | 2/1996 | Siedband et al. |
| 5,553,626 A | * | 9/1996 | Burger et al. ............ 600/590 |
| 5,586,562 A | * | 12/1996 | Matz ..................... 128/848 |
| 5,792,067 A | * | 8/1998 | Karell .................. 600/534 |
| 5,882,300 A | * | 3/1999 | Malinouskas et al. ....... 600/300 |
| 6,089,864 A | | 7/2000 | Buckner et al. |
| 6,762,687 B2 | * | 7/2004 | Perlman ............... 340/573.1 |

FOREIGN PATENT DOCUMENTS

| EP | 1 110 518 | | 6/2001 |
| EP | 1 110518 A1 | * | 6/2001 |

* cited by examiner

*Primary Examiner*—Patricia M Bianco
*Assistant Examiner*—Camtu T Nguyen
(74) *Attorney, Agent, or Firm*—Young & Thompson

(57) ABSTRACT

A device for preventing bruxism comprises a carrier (1) intended for receiving in a mouth of a user. The carrier (1) comprises at least a part (2,3) of an electronic biofeedback system. According to the invention the carrier comprises a jaw-shaped body which is adapted to lie only on an outer side against at least a part of a jaw of the user.

19 Claims, 5 Drawing Sheets

DEVICE FOR PREVENTING BRUXISM

CROSS REFERENCE TO RELATED APPLICATIONS

This application is the national stage of International Appl. No. PCT/NL2004/000895, filed Dec. 21, 2004, which claims priority of Netherlands Appl. No. 1025223, filed Jan. 13, 2004.

BACKGROUND OF THE INVENTION

1. Field of the Invention

The present invention relates to a device for preventing bruxism, comprising a carrier intended for receiving in a mouth of a user, which carrier comprises at least a part of an electronic bio-feedback system.

2. Related Art

Bruxism is an involuntary or subconscious para-function which takes place during the day as well as at night, and is manifested in a static or dynamic contact between the chewing surface complexes of the lower and upper jaw, wherein a pronounced neuromuscular activity occurs. These contacts do not form part of the normal functional physiology. Bruxism is also known as clenching and/or grinding of the teeth.

It is suspected that in the vast majority of cases bruxism is caused by stress resulting from suppressed flight response. Flight response is a normal instinctive phenomenon in nature, not only in animals but also in humans. During rest the parasympathetic part of the nervous system is active. A shock reaction disturbs this rest and will result in a flight response. There occurs here an acute shift from the parasympathetic part of the nervous system to the sympathetic part. Under the influence of hormones, such as (nor)adrenaline, cortisol, serotin and pheromones, blood is sent to the extremities to reinforce a flight response. When the flight attempt is successful or the danger has passed, the balance shifts back to the parasympathetic part of the nervous system and the rest state is eventually restored.

This instinctive behaviour still exists in humans, albeit that highly civilized man is able to suppress this flight response. This latter occurs for instance when someone finds himself in a traffic-jam on the way to an appointment. He/she wants to get away, but cannot do so. All physical phenomena linked to flight response now occur, but the eventual flight response is not effected. The sympathetic part of the nervous system is nevertheless in a full state of preparedness. At that moment the muscles of the head-neck area, i.e. the chewing muscles in particular, begin to play a crucial role.

Though tensioning of the chewing muscles a powerful biting action takes place, whereby small pain stimuli occur locally which can become manifest in, among other ways, pain in the teeth and molars, pain in the periodontium, pain in the jawbone around the roots of the teeth and molars, pain in the chewing muscles and pain in the jaw. These pain stimuli are per se hardly perceptible, but at a sufficient level will nevertheless result in suppressed flight response and the associated shift within the nervous system. The release of hormones induced by this flight response in turn causes tensioning of the chewing muscles, thereby resulting in a vicious circle which expresses itself in bruxism.

Bruxism is essentially a mechanical way of coping with stress which is experienced daily. In this respect bruxism is harmless and also functional. If however bruxism occurs too often this results in an increase of the chewing forces, whereby normal, intended chewing movements during eating are carried out with so much force that pain stimuli occur which in turn induce the above stated vicious circle. In addition to stress, normal daily occurrences will thus also provoke flight response or bruxism. The chewing force can herein increase significantly so that as a result of bruxism teeth and molars can be damaged and even muscular complaints, headaches and shoulder/neck disorders can result. Jaw joint disorders can eventually also occur, so-called arthrogenic disorders such as cracking jaw joints, in addition to earache and balance disorders. When a patient experiences such a wide variety of complaints to a lesser or greater degree, bruxism no longer has a functional and harmless nature but by now a more destructive one.

Bruxism therefore has both direct and indirect adverse effects on the state of health of a person. Firstly, bruxism causes damage to the teeth which is directly noticeable as such. Indirectly, bruxism however also has an adverse effect on the entire locomotor apparatus, i.e. muscles can tense up and joints can become overloaded or damaged. In addition, bruxism can cause disrupted sleep, with all the possible neurotic and psychological effects this entails.

The invention relates to a device which obviates or at least combats bruxism and therewith prevents or at least alleviates the adverse effects as described above. Such a device is already known from European patent EP 1.110.518. The device described herein comprises a carrier in the form of a splint which is received in the whole mouth. Situated on the splint are two anchoring elements which also serve as electrode and as antenna of the bio-feedback system which is partially integrated in the splint. As soon as the antenna detects an unintended, non-physiological activity of the teeth, for instance when the user is sleeping, this signal is generated to a control unit of the bio-feedback system, which in turn actuates a pulse generator. The pulse generator generates an electrical voltage and delivers this via the electrode as electrical stimulus to the jaw of the user in order to restore a state of rest therein. Bruxism can thus be nipped in the bud and the above stated adverse effects thereof on the condition of the user avoided. Bruxism will hereby decrease in the user and finally disappear completely. The device can otherwise also be applied as a preventive measure, particularly in patients who already suffer from bruxism but who have not yet developed any harmful consequences.

Although the known device is very effective per se in suppressing bruxism, the known device has the drawback that the carrier held inside the mouth by the user interferes in the internal mouth environment of the user and could occasionally result in complications. The known carrier must furthermore be modelled precisely in accordance with the internal anatomy of the mouth, which is not only time-consuming but also requires specialist knowledge and expertise. The present invention has for its object, among others, to provide a device of the type stated in the preamble which obviates these drawbacks to an at least considerable extent.

SUMMARY OF THE INVENTION

In order to achieve the stated object, a device of the type stated in the preamble is characterized according to the invention in that the carrier comprises a jaw-shaped body which is adapted to lie against at least a part of an outer side of a jaw of the user and therein leave a chewing or cutting surface at least substantially clear. Other than the carrier of the bio-feedback system in the known device, the carrier of the device according to the invention only lies against an outer side of the jaw and thus does not interfere in the internal mouth environment, the more so because the chewing and cutting surfaces are thereby left clear. It is herein noted that within the scope of the present application, the jaw is understood to include the jaw elements extending therefrom.

Such a jaw-shaped carrier is found in practice to require a considerably lower degree of precision and fit than a splint such as applied in the known device. Due to the open structure thereof, a thus formed carrier can afterwards be deformed and modified to the specific jaw shape of the user. It has therefore also been found that a dentist, or even the user him/herself, must be deemed able to effectively fit such a carrier. Because the carrier lies against an outer side of the jaw of the user, any impact thereby on the mouth environment inside the oral cavity of the user is furthermore avoided. The device according to the invention is thereby significantly simpler, more practical and less intrusive than the known device.

It is noted that a device of the type stated in the preamble based on a jaw-shaped carrier is per se known from for instance the American patent publication U.S. Pat. No. 5,490,520. Other than that according to the present invention, the carrier of the known device is however intended to extend completely over the chewing and cutting surfaces of the user in order to be able to detect a chewing pressure there as a signal for occurring bruxism. The inter-occlusal interference which is thus unavoidable results in an undesired load on the chewing joints and thereby occasionally in undesired complications. The present invention is able to avoid this.

In a preferred embodiment the device according to the invention is characterized in that the carrier is manufactured at least substantially from a thermoplastic material, in particular a synthetic material. By thus making use of a thermoplastic material in respect of the carrier, the carrier can be deformed as required afterward by heating the carrier to a temperature close to or above its softening point and then allowing it to cool again after the desired shape has been arranged therein. In a further particular embodiment, the device is herein characterized in that the carrier is permanently deformable at an increased temperature below about 100° C. In this case the described procedure can be carried out below the boiling point of water, which is particularly suitable for applications in a home situation by the user him/herself, who does not require any special equipment for this purpose other than a normally already available cooker.

During use the carrier lies against an outer side of at least a part of the jaw of the user, in particular against an outer side of his/her teeth. Both the lower and upper jaw can herein be used. In order to properly fix the device in the mouth here, particularly where use is made of the upper jaw, so that the bio-feedback system lies and makes contact at the correct position, a preferred embodiment of the device according to the invention is characterized in that the carrier is provided with at least one anchoring member which extends from the jaw-shaped body and which is able and adapted to enter into an at least temporary fixation with a jaw element of a user. The anchoring member engages on the jaw element of the user, preferably in the upper jaw between the fifth and sixth jaw element, and thereby fixes the device in the mouth of the user.

In a further embodiment, the device according to the invention has the feature that the anchoring member comprises an electrically conductive electrode of the bio-feedback system. By thus integrating multiple functions in the anchoring element the device can be kept relatively simple, which is not only advantageous for instance for manufacturing reasons, manufacturing costs, lifespan and operational reliability, but also limits the number of components in the mouth, which also enhances the ergonomics and wearer comfort of the device. A further contribution is made hereto in a further preferred embodiment of the device according to the invention, which is characterized in that the anchoring member comprises an electrically conductive signal sensor of the bio-feedback system.

An effective anchoring of the device to the jaw of the user requires a correct adjustment of the at least one anchoring member to the actual position of the jaw elements of the user. In order to keep this adjustment relatively simple, a further preferred embodiment of the device according to the invention has the feature that the anchoring member comprises an electrically conductive wire with a solid core of a bio-compatible metal. Such a solid metal wire herein protrudes like an antenna and can be given the correct size and shape with relatively simple tools. Any dentist, and even the user him/herself, must be considered capable hereof.

A further particular embodiment of the device according to the invention has the feature that the jaw-shaped body comprises an outer shell in which at least a part of the bio-feedback system is accommodated, and an inner shell which is formed at least close-fittingly in accordance with at least the part of the jaw of the user. In this case a separate anchoring of the carrier can be omitted because the close fit of the inner shell on the jaw of the user already provides sufficient fixation.

In order to enable delivery of a correcting stimulus to the jaw of the user, a further particular embodiment of the device according to the invention has the feature that the bio-feedback system comprises at least one electrically conductive electrode which extends from the outer shell and lies against the jaw of the user. During use such an electrode thus lies only against the outer side of the jaw of the user, so that insertion and removal of the device is not adversely affected thereby. This enhances convenience of use significantly. An effective adjustment of a length and orientation of the electrode suffices for an effective operation of the device. A good electrical contact is ensured in a further particular preferred embodiment of the device according to the invention, characterized in that the electrode has a resilient construction so as to lie resiliently against the jaw of the user.

If desired, the bio-feedback system can be placed partly outside the carrier, for instance to save space and weight and for safety reasons. This can relate to for instance an electric power source and a control unit. With a view hereto, a further embodiment of the device according to the invention has the feature that the carrier is provided with a first part of the bio-feedback system, and a second part of the bio-feedback system is placed outside the mouth, wherein both said parts are mutually connected by means of at least one electronic connection. A preferred embodiment of the device according to the invention has in this respect the feature that the electronic connection comprises a connecting cable which extends from the carrier on an outer side of the teeth. The connecting cable can serve on the one hand as power supply cable for the electronic components of the bio-feedback system which are placed in or on the carrier, and on the other for the desired signal transfer between these components and a control unit placed outside the carrier. Since according to this embodiment the connecting cable extends from the carrier on an outer side of the teeth, the cable does not form an obstacle to complete closing of the teeth of the user if desired, which enhances the wearer comfort of the device. With a view to an even greater wearer comfort, a further preferred embodiment of the device according to the invention is otherwise characterized in that the electronic connection is wireless. In this case the device requires no parts extending from the mouth at all, which not only leaves the jaw movement unimpeded but otherwise also guarantees complete freedom of movement of the user.

In respect of wireless signal transfer, a connection is for instance possible to existing, optionally standardized signal transmission protocols, such as in particular the bluetooth protocol. In respect of power supply to components of the bio-feedback system received in or on the carrier, a further particular embodiment of the device according to the invention has the feature that the carrier is provided with an electric power source which at least during operation provides an electric power supply to at least the part of the bio-feedback system received in the carrier. The power source for instance comprises an optionally exchangeable, optionally cast and optionally rechargeable battery or accumulator which is arranged in liquid-tight manner in the carrier. A preferred embodiment of the device according to the invention is also characterized herein in that the power source comprises at least one wirelessly rechargeable battery which is received in liquid-tight manner in the carrier. Use can be made of available means for wirelessly recharging the battery, for instance on the basis of induction currents, such as must be considered sufficiently well known to a person with ordinary skill in the art. The capacity of the battery can thus be limited to the capacity necessary for one or a few days, whereby the battery can be kept relatively small and light. To enable application wholly independently of an external power source or charging station, a further preferred embodiment of the device according to the invention has the feature that the power source comprises conversion means which are able and adapted to convert a jaw movement of the user into electricity. In this case the user himself produces the power supply of at least a part of the bio-feedback system, via the conversion means, from his/her chewing motions or bruxism.

All components of the device required in the mouth can per se be accommodated in or on the carrier and be inserted and removed together therewith. Particularly when placing the device care must herein be taken to position the carrier in the mouth correctly, particularly where the parts of the bio-feedback system responsible for the signal reception and stimulus delivery are concerned. A particular embodiment of the device according to the invention has the feature however that at least a part thereof is permanently connected to a jaw of the user, and in particular is integrated into a set of teeth of the user. These parts can for instance be anchoring elements facilitating a correct positioning of the carrier, but also optional electrodes for delivering stimuli and/or receiving muscle signals. Due to their permanent fixation in or on the jaw of the user the correct positioning thereof is ensured at all times.

DESCRIPTION OF THE SEVERAL VIEWS OF THE DRAWINGS

The invention will be further elucidated hereinbelow on the basis of a number of exemplary embodiments and an associated drawing. In the drawing.

The figures are drawn purely schematically and not to scale. Some dimensions in particular may be exaggerated to greater or lesser extent for the sake of clarity. Corresponding parts are designated in the figure with the same reference numeral.

DETAILED DESCRIPTION OF THE INVENTION

Figure 1:
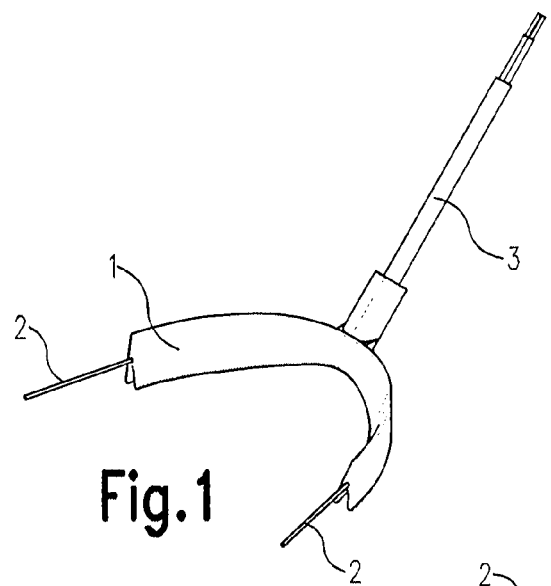
FIG. 1 shows a rear view of a first exemplary embodiment of a device for preventing bruxism according to the invention.

FIG. 1 shows an exemplary embodiment of a device for preventing bruxism according to the invention. In addition to the shown part, which is worn in the mouth of the user, the device also comprises an external part having therein, among other things, an electric power supply, a control unit with electronic memory in which operating software is loaded, and optional other components required or desired for operation of the device. This latter part is however not further shown in the figures for the sake of clarity, and is assumed to be sufficiently clear to a person with ordinary skill in the art.

The device comprises a jaw-shaped carrier 1 of a thermoplastic synthetic material, for instance a bio-compatible synthetic resin which is placed wholly against an outer side of an upper jaw of a user during use. One or more components 2 of a bio-feedback system are integrated into carrier 1. The bio-feedback system detects (chewing) muscle activity in the jaw of the user and, when this exceeds a predetermined value, transmits one or more electrical stimuli to the jaw of the user to induce an existing relax reflex therein. The chewing muscles subsequently relax and possible bruxing is thus stopped at an early stage. The signals received from the jaw muscles are in the order of a few nano-amperes and lie in a frequency range between 300 and 700 Hz. As soon as such a signal is detected for longer than 2-3 seconds, a correcting current pulse in the order of 9-12 volts is generated, typically for a millisecond.

Figure 4A:
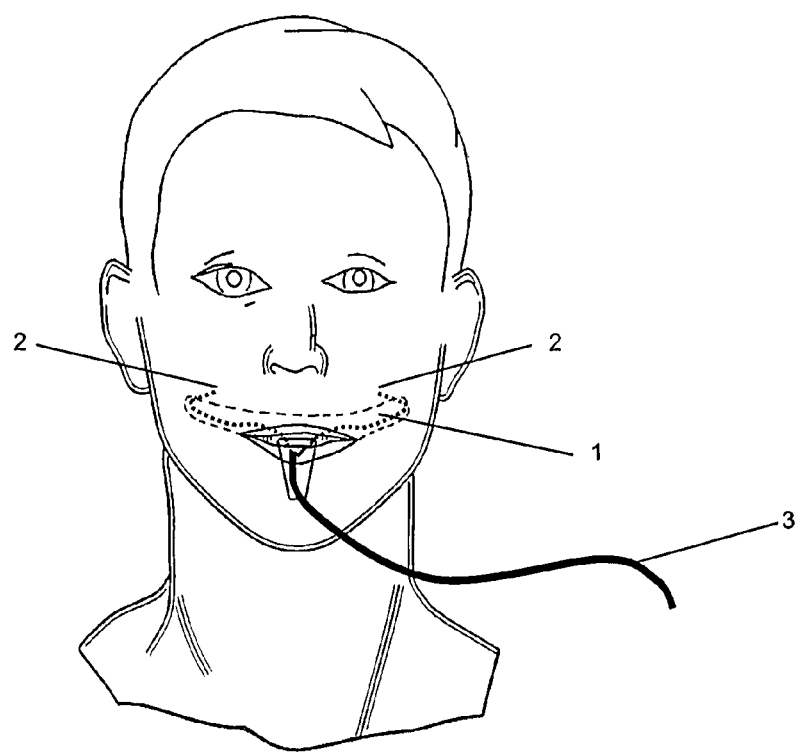
FIGS. 4A-4C show a positioning in the mouth of a user of an exemplary embodiment of a device for preventing bruxism according to the invention.
Figures 4B, 4C:
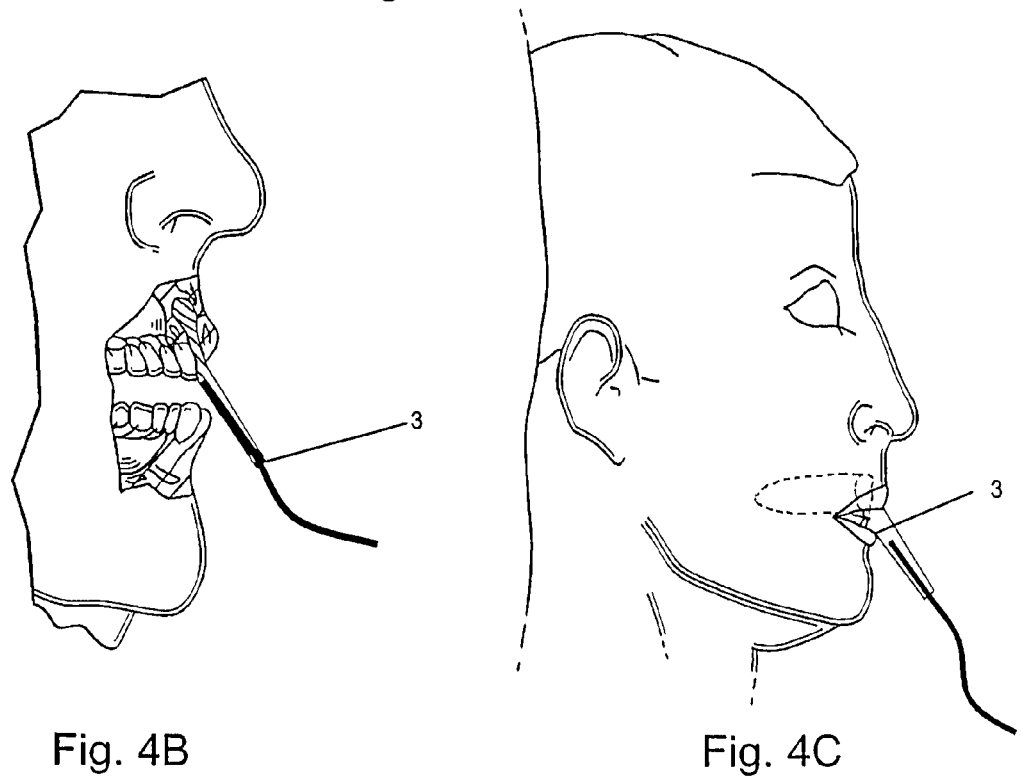
Figure 5:
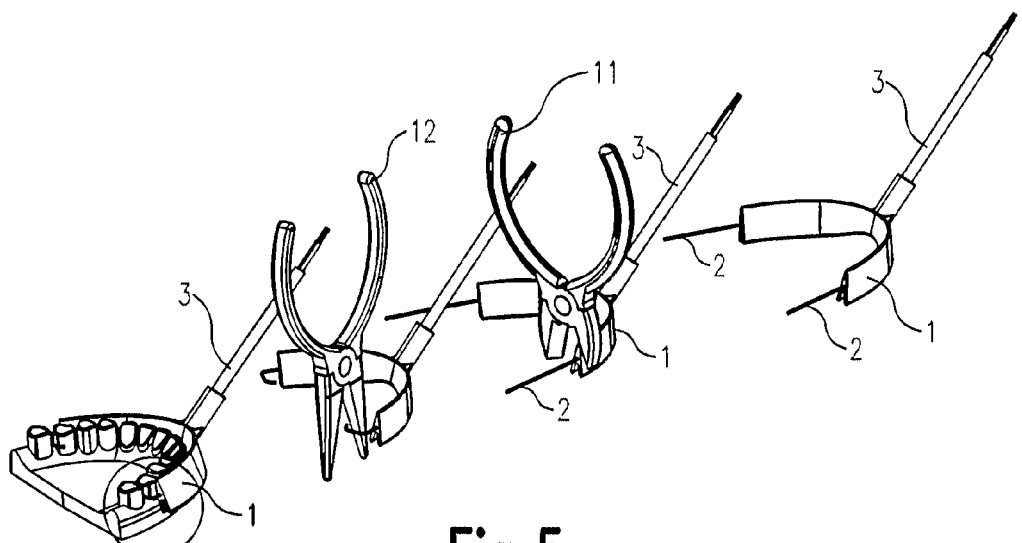
FIG. 5 shows successive stages of sizing and fitting the device of FIG. 1.
Figure 6:
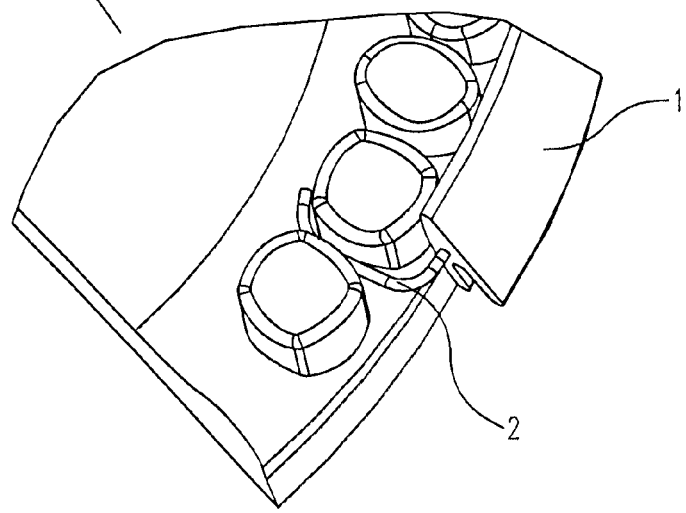
FIG. 6 shows an enlarged detail view of FIG. 5.

Carrier 1 comprises two anchoring members 2 and is adapted to lie against the teeth of the user on a buccal side, as shown in FIGS. 4-4C. Anchoring members 2 serve in the first place to fix carrier 1 to the teeth and are formed from a wire with a solid core of bio-compatible material, in this example orthodontic steel. As shown schematically in successive stages in FIG. 5, such a wire can be cut to size relatively easily using a simple pair of pliers or other tool 11 and bent into the desired shape with a similar tool 12. As shown in FIG. 6, the anchoring members are eventually situated at the position of jaw elements P2SD,P2SS,M1SD and M1SS, which guarantees good operation in practice, although fixing is also possible at other positions. The anchoring members protrude like antennas on either side from the ends of carrier 1 but are otherwise embedded in liquid-tight manner in the material of the carrier to prevent corrosion or other destructive effect thereon.

As well as for such an accurate fixing of the device in the mouth, anchoring members 2 also serve as signal sensor for detecting said muscle activity and as electrode for generating the correcting electrical stimulus. In order to measure the muscle activity, members 2 operate as a receiving antenna for receiving an electro-muscular signal from the chewing muscles. The exact position of electrodes 2 herefor is found in practice not to be very critical. By administering an electrical pulse as stimulus at the correct position via the same electrodes 2, the detected para-functional muscle activity is interrupted and a relax reflex is induced, whereby the chewing muscles return to a state of rest. This is the same reflex which occurs when one bites unintentionally on something hard, for instance a hard piece in a currant bun. Anchoring members 2 thus have a three-fold function. Through wearing the device and receiving an electrical pulse each time there are signs of bruxism, the user becomes conditioned, whereby the bruxism behaviour will eventually stop completely. By using the device to a sufficient extent and for a long period, bruxism can thus be overcome and the neuromuscular equilibrium of the head/neck area restored. The chewing force then has its normal physiological value again and the patient is rid of the above described adverse effects of bruxism. Because the vicious circle of bruxism also described above is broken and physiologically the body is functioning normally again, existing, already contracted disorders also have the opportunity to disappear.

Electrodes 2 are connected to the external part of the bio-feedback system with electric power supply by means of a connecting cable 3. Carrier 1 is preferably worn on the upper teeth, as shown in FIGS. 4A-4C, wherein connecting cable 3 protrudes from the mouth. Because connecting cable 3 is connected to the buccal side of carrier 1, cable 3 does not here impede full closing of the jaws. If desired, use can also be made of an alternative embodiment wherein a wireless connection is applied for the signal transfer and an electric power source is integrated into the carrier. The embodiment shown here is however found to be sufficiently ergonomic in practice not to limit the user in his/her freedom of movement and not disturb his/her sleep.

Figures 2A, 2B:
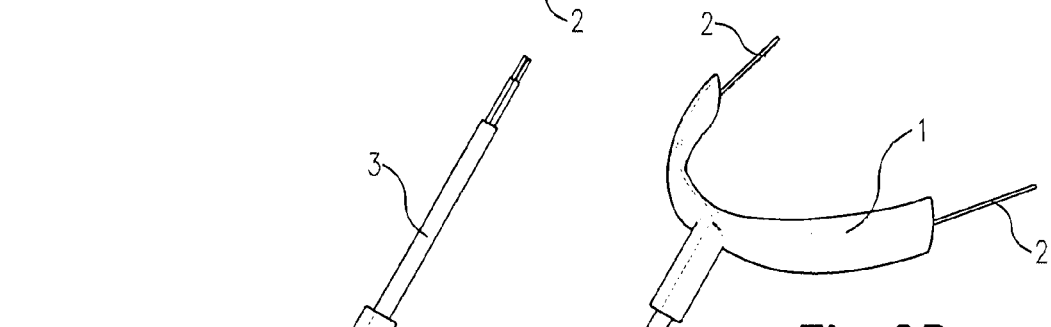
FIGS. 2A-2B show respectively a rear and front view of a second exemplary embodiment of a device for preventing bruxism according to the invention.
Figure 3:
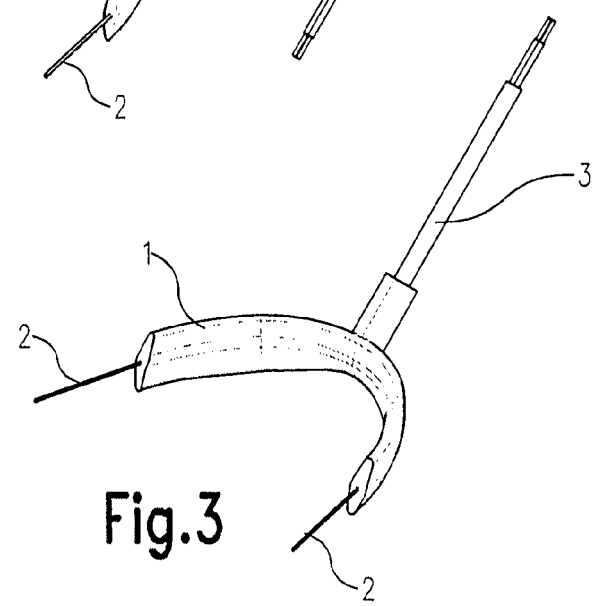
FIG. 3 shows a rear view of a third exemplary embodiment of a device for preventing bruxism according to the invention.

As is shown in FIG. 1, the jaw-shaped carrier 1 has a substantially V-shaped cross-section. Use can also be made of alternatively shaped carrier bodies instead, such as the second exemplary embodiment of a device for preventing bruxism according to the invention shown in FIGS. 2A-2B, in respectively rear view and front view, wherein use is made of a substantially oval cross-section. This device is otherwise the same as that of FIG. 1. This latter also applies for the embodiment shown in FIG. 3, wherein use is made of a more angular cross-section. The design can thus be varied for optimum fitting to the jaw-line of the user.

Figure 7:
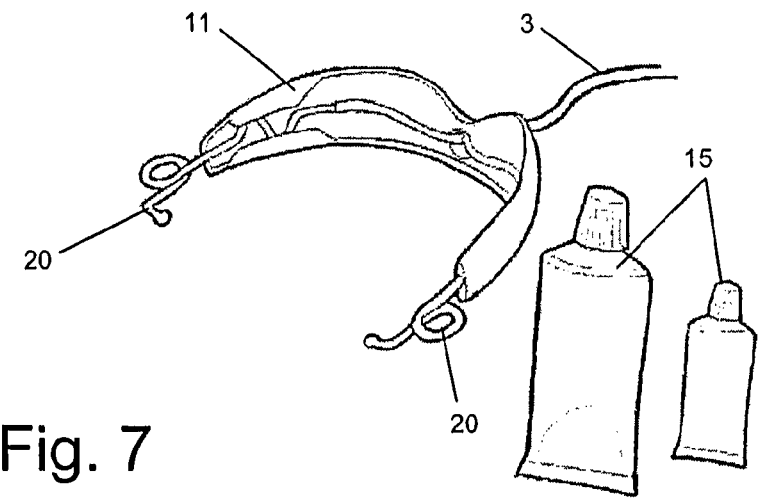
FIGS. 7-12 show successive stages of fitting a third embodiment of a device according to the invention.

A third embodiment of a device for preventing bruxism according to the invention is shown in FIG. 7 and further. The carrier of the device which must be worn in the mouth comprises in this case an outer shell 11 in which the part of the bio-feedback system is integrated. This part comprises, among other components, two electrodes 20 which extend on either side thereof, and a connecting cable 3 which leads to a base station placed outside the mouth. The outer shell is manufactured from a relatively form-retaining, bio-compatible synthetic material. Use is advantageously made here of a limited number of standard sizes which only approximate the size of the jaw of the user.

Figure 8:
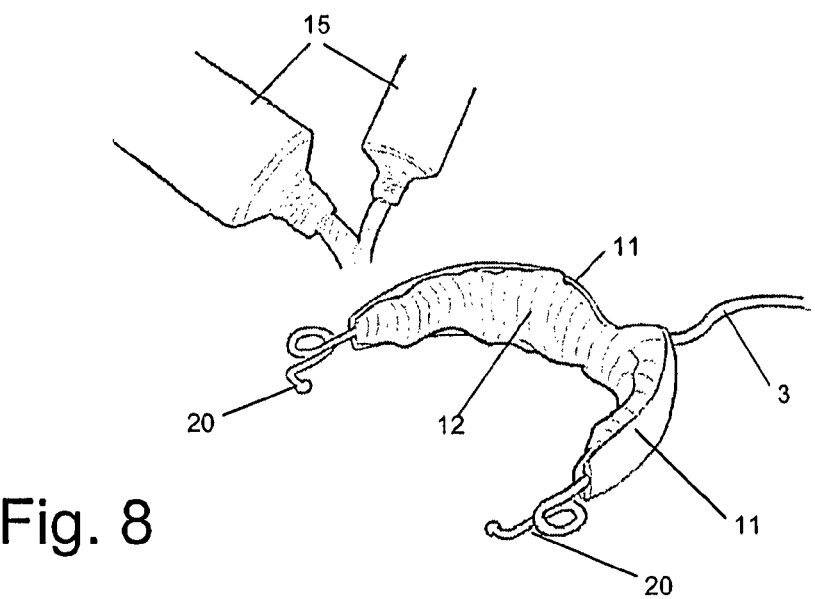
Figure 9:
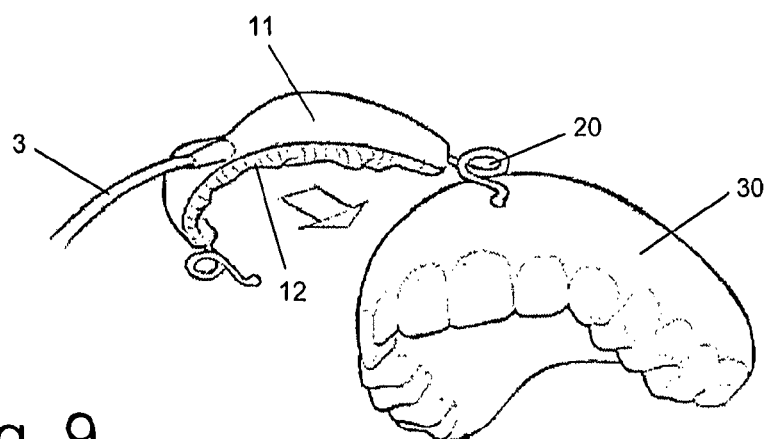
Figure 10:
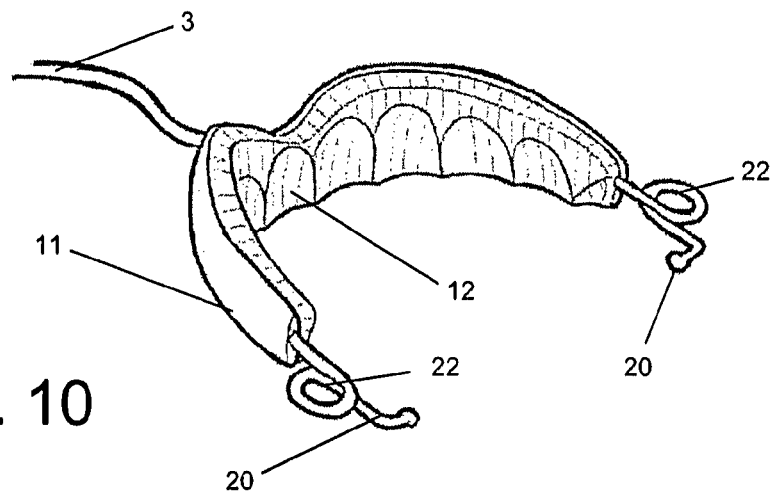
Figure 11:
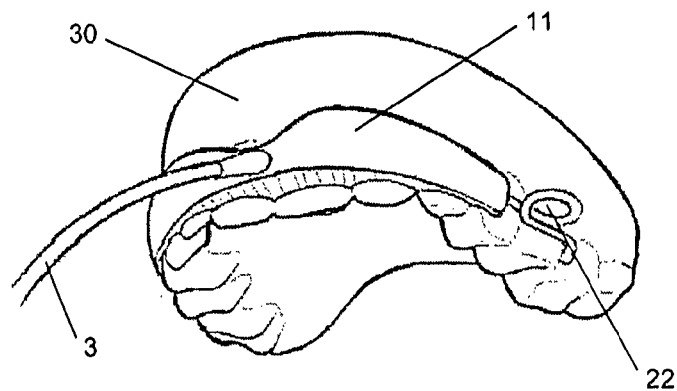

For fitting on the jaw 30 of the user, the carrier comprises an inner shell 12, see FIG. 8, which is arranged to the size of the upper teeth 30, see FIG. 9, of the user using a two-component paste 15. For this purpose the paste 15 is applied in a liberal quantity in outer shell 11, see FIG. 8, and pressed firmly against the upper teeth 30 of the user, see FIG. 9. The viscous paste will herein set precisely in accordance with the shape of the teeth of the user. After being removed and cured, an outer shell 12 thus results, see FIG. 10, which connects close-fittingly to the teeth of the user. This precise fit provides a close fit whereby carrier 11,12 remains fixedly attached against the upper jaw of the user without further anchoring means being required, see FIG. 11. Instead of a two-component paste, use can also be made of similar other materials for this purpose, particularly a thermally permanently deformable thermoplastic and other deformable materials, which cure under the influence of optionally visible light, radiation or in other manner so as to take on a permanent form.

Figure 12:
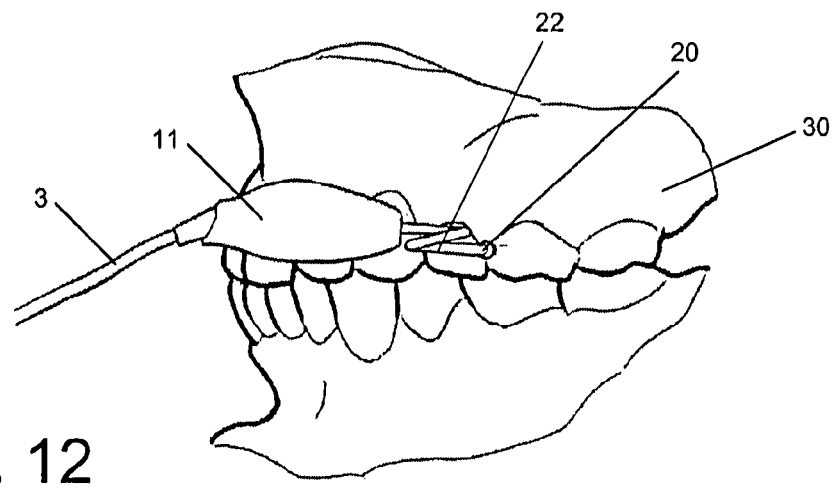

Electrodes 2 are formed and oriented such that they lie accurately at the correct location against jaw 30 of the user when carrier 11,12 is fitted on teeth 30, see FIG. 12. A correcting stimulus has been found to be most effective at this location. A resilient turn 22 in electrode 2 herein provides extra pressure at the intended location and thereby enhances an effective electrical connection at that position.

Although the invention has been further elucidated above with reference to only a few exemplary embodiments, it will be apparent that the invention is in no way limited to the given exemplary embodiments. On the contrary, many variations and embodiments are still possible within the scope of the invention for a person with ordinary skill in the art.

The invention claimed is:

1. A device for preventing bruxism, comprising a carrier intended for receiving in a mouth of a user, which carrier comprises at least a part of an electronic bio-feedback system,
wherein the carrier comprises a jaw-shaped body which is adapted to lie against at least a part of an outer side of a jaw of the user and therein leave a chewing or cutting surface at least substantially clear, and the carrier is provided with at least one anchoring member which extends from the jaw-shaped body and which is able and adapted to enter into an at least temporary fixation with a jaw element of a user and the anchoring member comprises an electrically conductive wire with a solid core of a bio-compatible metal.

2. The device as claimed in claim 1, wherein the carrier is manufactured at least substantially from a thermoplastic material, in particular a synthetic material.

3. The device as claimed in claim 2, wherein the carrier is permanently deformable at an increased temperature below about 100° C.

4. The device as claimed in claim 3, wherein the jaw-shaped body comprises an outer shell in which at least the part of the bio-feedback system is accommodated, and an inner shell which is formed at least close-fittingly in accordance with at least the part of the jaw of the user.

5. The device as claimed in claim 1, wherein the anchoring member comprises an electrically conductive electrode of the bio-feedback system.

6. The device as claimed in claim 5, wherein the anchoring member comprises an electrically conductive signal sensor of the bio-feedback system.

7. The device as claimed in claim 1, wherein at least the part is permanently connected to a jaw of the user, and in particular is integrated into a set of teeth of the user.

8. The device as claimed in claim 1, wherein the jaw-shaped body comprises an outer shell in which at least the part of the bio-feedback system is accommodated, and an inner shell which is formed at least close-fittingly in accordance with at least the part of the jaw of the user.

9. The device as claimed in claim 8, wherein the bio-feedback system comprises at least one electrically conductive electrode which extends from the outer shell and lies against the jaw of the user.

10. The device as claimed in claim 9, wherein the electrode has a resilient construction so as to lie resiliently against the jaw of the user.

11. The device as claimed in claim 1, wherein the carrier is provided with a first part of the bio-feedback system, and a second part of the bio-feedback system is placed outside the mouth, wherein both said parts are mutually connected by means of at least one electronic connection.

12. The device as claimed in claim 11, wherein the electronic connection comprises a connecting cable which extends from the carrier on an outer side of the teeth.

13. The device as claimed in claim 11, wherein the electronic connection is wireless.

14. The device as claimed in claim 1, wherein the carrier is provided with an electric power source which at least during operation provides an electric power supply to at least the part of the bio-feedback system received in the carrier.

15. The device as claimed in claim 14, wherein the power source comprises at least one wirelessly rechargeable battery which is arranged in liquid-tight manner in the carrier.

16. The device as claimed in claim 14, wherein the power source comprises conversion device which are able and adapted to convert a jaw movement of the user into electricity.

17. The device as claimed in claim 1, wherein the anchoring member comprises an electrically conductive signal sensor of the bio-feedback system.

18. The device as claimed in claim 17, wherein the anchoring member comprises an electrically conductive wire with a solid core of a bio-compatible metal.

19. A device for preventing bruxism, comprising a carrier intended for receiving in a mouth of a user, which carrier comprises at least a part of an electronic bio-feedback system, wherein the carrier comprises a jaw-shaped body which is adapted to lie against at least a part of an outer side of a jaw of the user and therein leave a chewing or cutting surface at least substantially clear, and the carrier is provided with at least one anchoring member which extends from the jaw-shaped body and which is able and adapted to enter into an at least temporary fixation with a jaw element of a user and the anchoring member comprises an electrically conductive signal sensor of the bio-feedback system which comprises an electrically conductive wire with a solid core of a bio-compatible metal.

* * * * *